(12) United States Patent
Banju et al.

(10) Patent No.: US 10,569,203 B2
(45) Date of Patent: Feb. 25, 2020

(54) FILTRATION FILTER DEVICE

(71) Applicant: Murata Manufacturing Co., Ltd., Nagaokakyo-shi, Kyoto-fu (JP)

(72) Inventors: Masaru Banju, Nagaokakyo (JP); Junko Watanabe, Nagaokakyo (JP); Takashi Kondo, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 0 days.

(21) Appl. No.: 16/129,854

(22) Filed: Sep. 13, 2018

(65) Prior Publication Data

US 2019/0009197 A1 Jan. 10, 2019

Related U.S. Application Data

(63) Continuation of application No. PCT/JP2017/016045, filed on Apr. 21, 2017.

(30) Foreign Application Priority Data

May 6, 2016 (JP) .................................. 2016-093427

(51) Int. Cl.
*B01D 35/30* (2006.01)
*B01D 71/02* (2006.01)
(Continued)

(52) U.S. Cl.
CPC ............. *B01D 35/30* (2013.01); *B01D 29/05* (2013.01); *B01D 29/58* (2013.01); *B01D 63/06* (2013.01);
(Continued)

(58) Field of Classification Search
CPC ........ B01D 35/30; B01D 29/58; B01D 29/05; B01D 63/06; B01D 63/08; B01D 71/02;
(Continued)

(56) References Cited

U.S. PATENT DOCUMENTS

2003/0192363 A1* 10/2003 Adiletta ............... B01D 46/543
73/28.04
2016/0041075 A1 2/2016 Kamba et al.
(Continued)

FOREIGN PATENT DOCUMENTS

JP H03109043 U 11/1991
JP H07136411 A 5/1995
(Continued)

OTHER PUBLICATIONS

International Search Report issued for PCT/JP20171016045, dated Jul. 25, 2017.
(Continued)

*Primary Examiner* — Madeline Gonzalez
(74) *Attorney, Agent, or Firm* — Arent Fox LLP

(57) ABSTRACT

A filtration filter device that enables an object filtered and left on a filtration filter to be more readily observed is provided. The filtration filter device includes a filtration filter that filters an object contained in a fluid, a holding member that holds an outer circumferential portion of the filtration filter, and a tubular member that is removably mounted on the holding member such that a hollow portion that serves as a channel through which the fluid flows faces at least a part of a main surface of the filtration filter.

17 Claims, 12 Drawing Sheets

(51) Int. Cl.
- *B01D 63/06* (2006.01)
- *B01D 63/08* (2006.01)
- *G01N 1/40* (2006.01)
- *B01D 29/58* (2006.01)
- *B01D 29/05* (2006.01)
- *G01N 1/10* (2006.01)

(52) U.S. Cl.
CPC .............. *B01D 63/08* (2013.01); *B01D 71/02* (2013.01); *G01N 1/4077* (2013.01); *B01D 63/087* (2013.01); *B01D 71/022* (2013.01); *B01D 2201/0423* (2013.01); *G01N 1/10* (2013.01); *G01N 2001/4088* (2013.01)

(58) Field of Classification Search
CPC ................ B01D 71/022; B01D 63/087; B01D 2201/0423; G01N 1/4077; G01N 2001/4088; G01N 1/10
USPC .................................. 210/445, 435, 439, 446
See application file for complete search history.

(56) References Cited

U.S. PATENT DOCUMENTS

| | | |
|---|---|---|
| 2016/0054223 A1 | 2/2016 | Kamba et al. |
| 2017/0203260 A1 | 7/2017 | Kondo et al. |

FOREIGN PATENT DOCUMENTS

| | | |
|---|---|---|
| JP | H0889720 A | 4/1996 |
| JP | H08290019 A | 11/1996 |
| JP | 2000046702 A | 2/2000 |
| JP | 2005214785 A | 8/2005 |
| JP | 2007304016 A | 11/2007 |
| JP | 2009079980 A | 4/2009 |
| WO | 2014192917 A1 | 12/2014 |
| WO | 2017022419 A1 | 2/2017 |

OTHER PUBLICATIONS

Written Opinion of the International Searching Authority issued for PCT/JP2017/016045, dated Jul. 25, 2017.

* cited by examiner

FILTRATION FILTER DEVICE

CROSS REFERENCE TO RELATED APPLICATIONS

The present application is a continuation of PCT/JP2017/016045 filed Apr. 21, 2017, which claims priority to Japanese Patent Application No. 2016-093427, filed May 6, 2016, the entire contents of each of which are incorporated herein by reference.

TECHNICAL FIELD

The present disclosure relates to a filtration filter device that filters an object contained in a fluid.

BACKGROUND

For example, a conventional filtration filter device is disclosed in Patent Document 1 (identified below), which is known as a type of filtration filter device.

The filtration filter device in Patent Document 1 includes a filtration filter that filters an object contained in a fluid, and a housing member that has an interior space in which the filtration filter is disposed. The housing member includes an inflow-side projecting portion via which the fluid flows into the interior space and an outflow-side projecting portion via which the fluid that has passed through the filtration filter flows out from the interior space.

Patent Document 1: Japanese Unexamined Patent Application Publication No. 2007-304016.

However, from perspective of observation of the object filtered and left on the filtration filter, the existing filtration filter device as disclosed in Patent Document 1 leaves room for improvement.

SUMMARY OF THE INVENTION

It is an object of the exemplary embodiments of the present disclosure to provide a filtration filter device that enables an object filtered and left on a filtration filter to be more readily observed.

To achieve the stated object, a filtration filter device according to an exemplary embodiment is disclosed that includes a filtration filter that filters an object to be filtered that a fluid contains, a holding member that holds an outer circumferential portion of the filtration filter, and a tubular member that is mounted on the holding member such that a hollow portion that serves as a channel through which the fluid flows faces at least a part of a main surface of the filtration filter. The tubular member is removably mounted on the holding member.

The filtration filter device according to the exemplary embodiment of the present disclosure enables the object filtered and left on the filtration filter to be more readily observed.

DETAILED DESCRIPTION OF EMBODIMENTS

Figure 1:
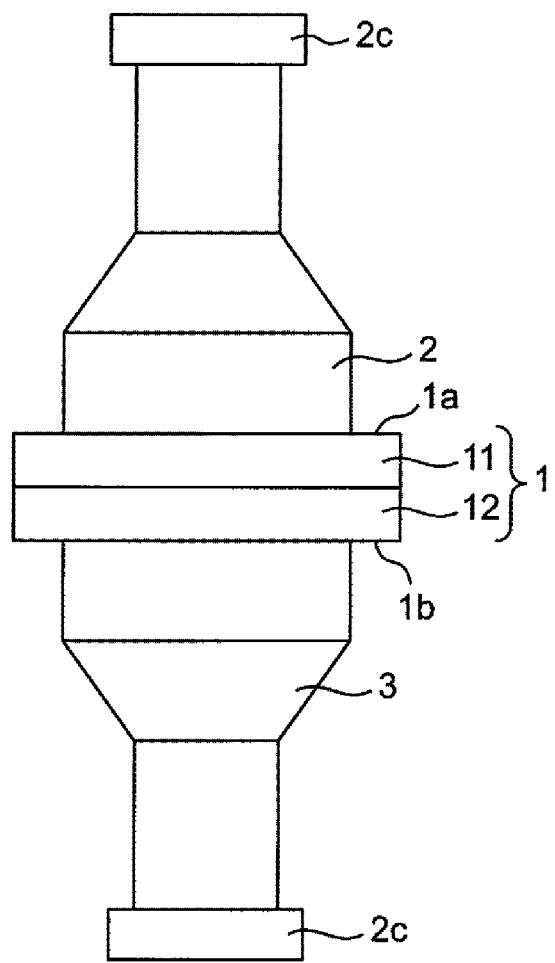
FIG. 1 is a side view of the overall structure of a filtration filter device according to a first exemplary embodiment.

Generally speaking, the present inventors have seriously considered how to more readily observe an object filtered and left on a filtration filter and have identified the following considerations.

In an existing filtration filter device, a filtration filter is disposed in the interior space of a housing member, and accordingly, the filtration filter can be directly observed only via an inflow-side projecting portion and an outflow-side projecting portion. To observe the object filtered and left on the filtration filter, for example, it can be through that, after a fluid is caused to flow in an opposite direction for backwashing, a mixture of the fluid that is discharged from the inflow-side projecting portion and the object filtered is observed. In this case, however, the object filtered may deform.

To prevent this result, for example, it can be thought that an inflow-side housing member that includes the inflow-side projecting portion and an outflow-side housing member that includes the outflow-side projecting portion are isolated from each other, and the filtration filter is removed from the interior space for observation. In this case, however, the object filtered can be unintentionally lost from the filtration filter or the amount thereof decreases due to a shake or unintentional movement of the filtration filter when the filtration filter is removed. Moreover, when the filtration filter is formed of a thin metallic porous film, it is practically difficult for a user to directly dispose the metallic porous film in the interior space of the housing member and to directly remove the metallic porous film from the interior space.

As a result of serious consideration based on the above knowledge, the present inventors have found the following. A holding member is configured to hold an outer circumferential portion of a filtration filter, and a tubular member is configured to be removably mounted on the holding member. This configuration enables an object filtered to be more readily observed. With such a structure, mounting the tubular member on the holding member enables the fluid to be supplied to the filtration filter via the tubular member to filter the object to be filtered. In addition, removing the tubular member from the holding member enables the object filtered and left on the filtration filter to be directly observed while the holding member holds the outer circumferential portion of the filtration filter. At this time, the holding member can maintain a state in which a tensile force is applied to the filtration filter, and accordingly, the filtration filter can be inhibited from shaking and unintentionally moving. Since the state in which the tensile force is applied to the filtration filter is maintained, focus can be readily adjusted when the object filtered and left on the filtration filter is observed with, for example, an electron microscope. Furthermore, a user can move the filtration filter by holding the holding member, and handling is easy. Accordingly, the above structure enables the object filtered and left on the filtration filter to be more readily observed (and analyzed with, for example, an X-rays).

In consideration for these matters, a filtration filter device is provided according to an exemplary embodiment that includes a filtration filter that filters an object contained in a fluid, a holding member that holds an outer circumferential portion of the filtration filter, and a tubular member that is mounted on the holding member such that a hollow portion that serves as a channel through which the fluid flows faces at least a part of a main surface of the filtration filter. The tubular member is removably mounted on the holding member.

According to the configuration of the exemplary embodiment, removing the tubular member from the holding member enables the object filtered and left on the filtration filter to be directly observed while the holding member holds the outer circumferential portion of the filtration filter. Consequently, the object filtered and left on the filtration filter can be more readily observed.

Moreover, the filtration filter preferably includes a metallic porous film. The use of the metallic porous film enables both of the main surfaces thereof to be inhibited or prevented from having irregularities. Accordingly, focus can be more readily adjusted when the object filtered and left on the filtration filter is observed with, for example, an electron microscope.

The holding member preferably includes a first frame member and a second frame member that are configured to interpose the outer circumferential portion of the filtration filter therebetween. With this structure, the filtration filter can be readily replaced after the first frame member and the second frame member are separated from the outer circumferential portion.

The first frame member and the second frame member preferably interpose the outer circumferential portion of the filtration filter at a position away from a central plane with respect to a thickness direction of the holding member in the thickness direction. With this structure, for example, in the case where the filtration filter is located away from the central plane with respect to the thickness direction of the holding member toward the side on which the fluid is supplied, focus can be readily adjusted when the object filtered and left on the filtration filter is observed with, for example, an electron microscope. For example, in the case where the filtration filter is located away from the central plane with respect to the thickness direction of the holding member toward the side on which the fluid is discharged, the volume of a space that is surrounded by the holding member and the filtration filter can be increased. This enables the fluid to be inhibited from overflowing from the space when the tubular member is removed and enables the filtration filter to filter the object to be filtered with more certainty.

The holding member preferably includes an annular projecting portion that projects in the thickness direction from one main surface thereof or the other main surface, and the filtration filter is preferably disposed inside the projecting portion. With this structure, focus can be more readily adjusted when the object filtered and left on the filtration filter is observed with, for example, an electron microscope. In addition, the volume of the space that is surrounded by the holding member and the filtration filter can be further increased. This enables the filtration filter to filter the object to be filtered with more certainty.

The filtration filter is preferably flush with or substantially flush with an opening plane that is defined by an end portion of the annular projecting portion. With this structure, focus can be more readily adjusted when the object filtered and left on the filtration filter is observed with, for example, an electron microscope. In addition, the volume of the space that is surrounded by the holding member and the filtration filter can be further increased. This enables the filtration filter to filter the object to be filtered with more certainty.

In addition, the outer circumferential portion of the filtration filter preferably includes a first bend and a second bend and is preferably interposed between the first frame member and the second frame member so as to include a striped projection between the first bend and the second bend. With this structure, the filtration filter, which includes the striped projection between the first bend and the second bend, can increase frictional forces between the first frame member and the outer circumferential portion of the filtration filter and between the second frame member and the outer circumferential portion of the filtration filter. This increases forces at which the first frame member and the second frame member hold the filtration filter without increasing the number of components.

The striped projection is preferably one of a plurality of striped projections disposed between the first bend and the second bend, and the plurality of striped projections preferably extend in irregular directions. This structure can increase the frictional forces between the first frame member and the outer circumferential portion of the filtration filter and between the second frame member and the outer circumferential portion of the filtration filter and further increase the forces at which the first frame member and the second frame member hold the filtration filter.

Yet further, it is preferable that the tubular member configured to be removably mounted on one main surface of the holding member, and another tubular member be removably mounted on the other main surface. With this structure, for example, the hollow portion of the tubular member can function as a fluid inflow channel, and the hollow portion of the other tubular member can function as a fluid discharge channel. This is also advantageous when the fluid is caused to flow in an opposite direction for backwashing. In addition, for example, a symmetric structure in the vertical direction with the filtration filter centered can be formed, and it is not necessary for a user to be careful that which portion is the fluid inflow channel or the fluid discharge channel when the filtration filter device is used.

The tubular member preferably includes a Luer lock connector. This structure achieves, for example, direct mounting on a Luer lock syringe and improves usability.

The filtration filter device preferably includes a plurality of the holding members that are configured to be removably mounted on each other. With this structure, filtration filters can be readily installed in and removed from the filtration filter device, and the usability can be improved. For example, the object to be filtered can be filtered with the filtration filters, and accordingly, filtering efficiency can be improved. In the case where the diameter of each through-hole is changed between the filtration filters, objects to be filtered having different sizes can be classified.

Moreover, the holding member preferably includes at least three or more frame members that are preferably configured to interpose the outer circumferential portion of the filtration filter between the adjoining frame members. With this structure, filtration filters can be readily installed in and removed from the filtration filter device, and the usability can be improved. In the case where the diameter of each through-hole is changed between the filtration filters, the objects to be filtered having different sizes can be classified.

It is preferable that the tubular member have an internal thread, the holding member have an external thread, and the tubular member be removably mounted on the holding member with the external thread being screwed in the internal thread. With this structure, the tubular member can be more readily mounted on and removed from the holding member, and the liquid can be more successfully inhibited from leaking.

It is preferable that the tubular member is configured to be removably mounted on one main surface of the holding member, another tubular member be removably mounted on the other main surface, the tubular member be mounted on the one main surface of the holding member and the other tubular member be mounted on the other main surface of the holding member when the tubular members are rotated in opposite directions to screw an external thread that is formed on one main surface side of the holding member and an external thread that is formed on the other main surface side of the holding member in the corresponding internal threads. With this structure, when the tubular member is removed from the holding member, the other tubular member can be inhibited from being rotated together with the tubular member and unintentionally removed from the holding member.

In an exemplary aspect, it is preferable that $t/P \geq 1$ hold, where t is a length of the internal thread or the external thread in a direction of screwing, and P is a pitch of the internal thread or the external thread. With this configuration, when pure water flows to the filtration filter at a pressure of 1 kPa (kilopascal), a liquid leak can be inhibited from occurring between the external thread and the internal thread.

Moreover, in an another exemplary aspect, it is preferable that $t/P \geq 2$ hold, where t is the length of the internal thread or the external thread in the direction of screwing, and P is the pitch of the internal thread or the external thread. When pure water flows to the filtration filter at a high pressure of 100 kPa, a liquid leak can be inhibited from occurring between the external thread and the internal thread.

In addition, the pitch of the internal thread or the external thread is preferably 0.3 mm or more. This configuration improves work efficiency when the external thread is screwed in the internal thread.

The length of the internal thread or the external thread in the direction of screwing is preferably 4.0 mm or less. For example, when the object to be filtered is a cell, this configuration shortens the time during which the external thread is screwed in the internal thread (within 30 seconds) and inhibits the activity of the cell from decreasing.

Exemplary embodiments of the present disclosure will hereinafter be described with reference to the drawings.

First Exemplary Embodiment

Figure 2:
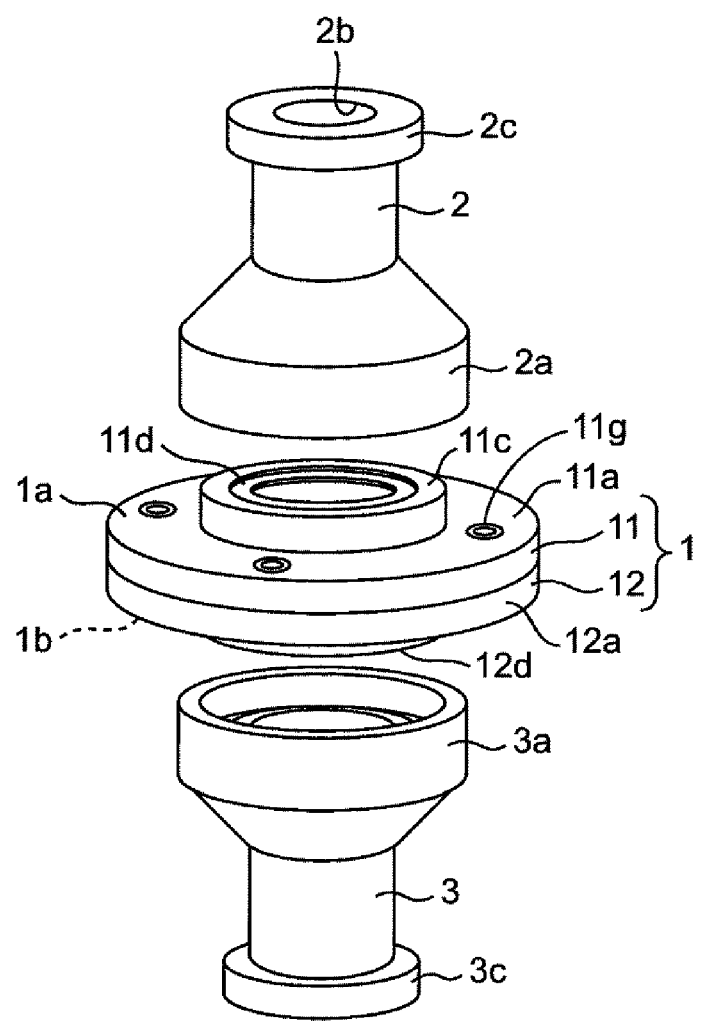
FIG. 2 is an exploded perspective view of a part of the filtration filter device in FIG. 1.
Figure 3:
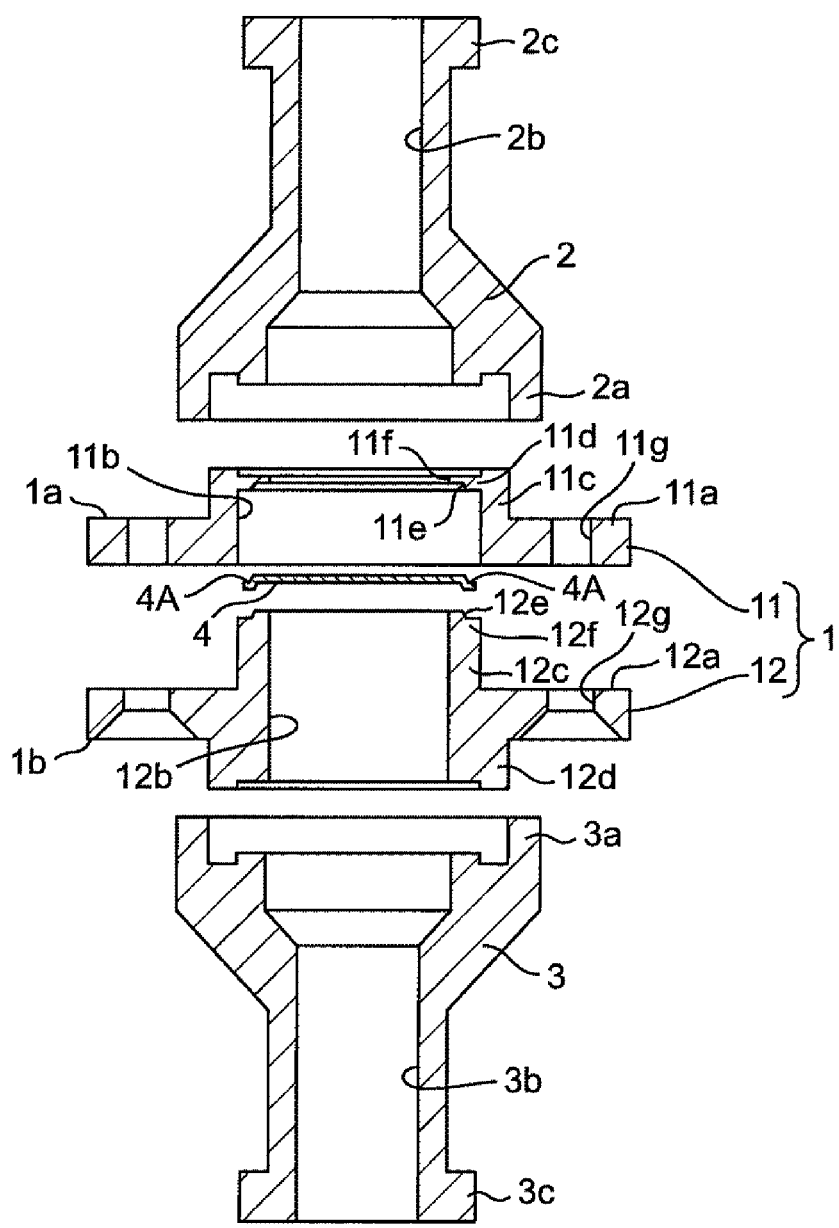
FIG. 3 is an exploded sectional view of the filtration filter device in FIG. 1.
Figure 4:
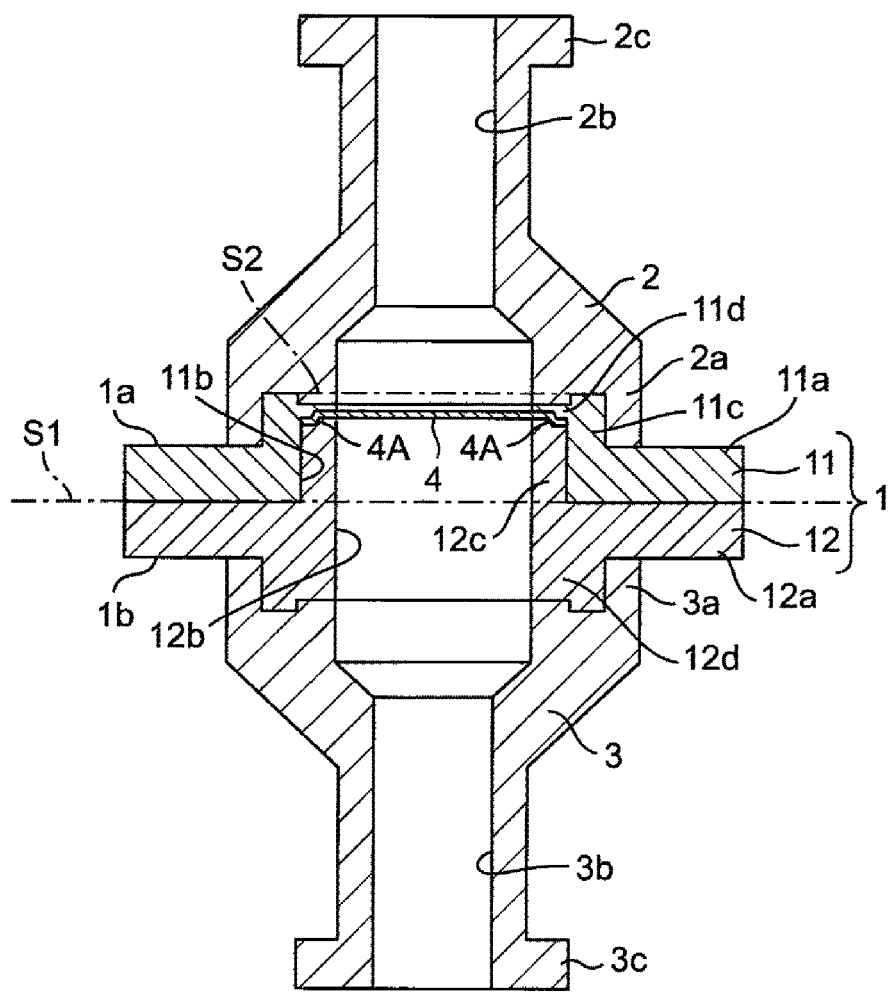
FIG. 4 is a sectional view of an assembly of the filtration filter device in FIG. 1.
Figure 5:
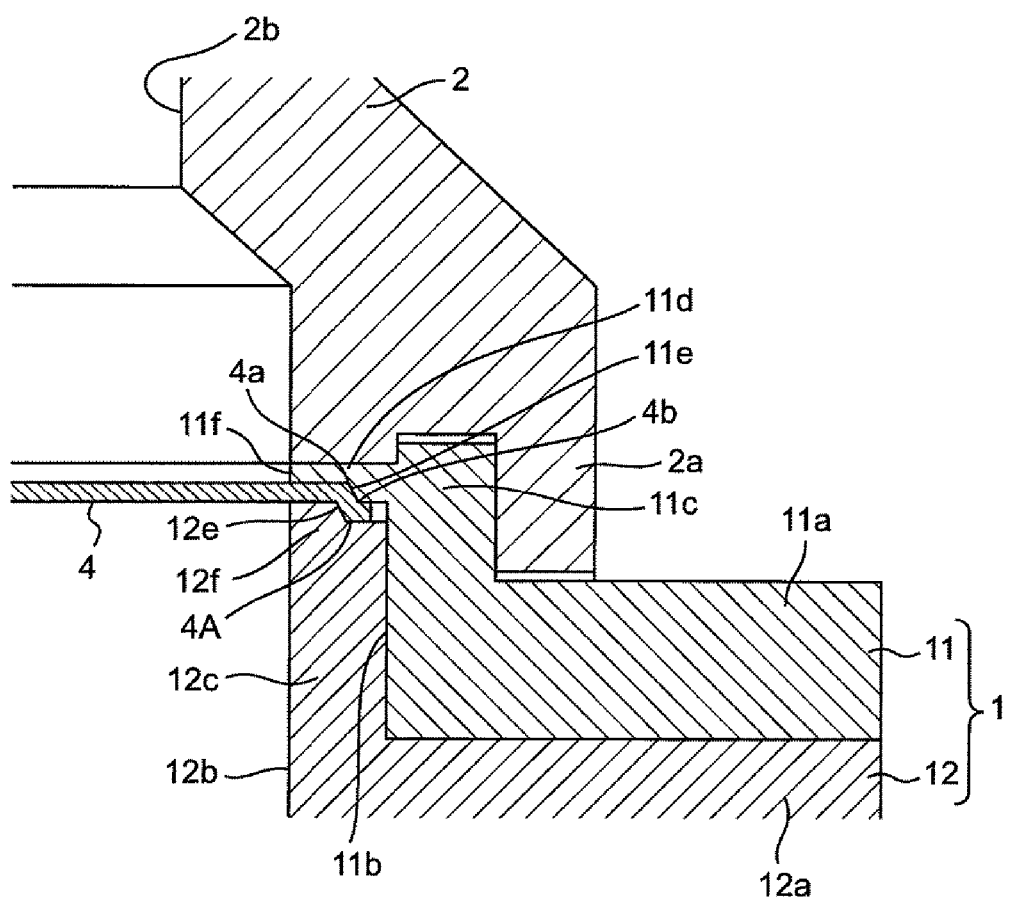
FIG. 5 is an enlarged sectional view of a part of FIG. 4.

FIG. 1 is a side view of the overall structure of a filtration filter device according to a first exemplary embodiment. FIG. 2 is an exploded perspective view of a part of the filtration filter device in FIG. 1. FIG. 3 is an exploded sectional view of the filtration filter device in FIG. 1. FIG. 4 is a sectional view of an assembly of the filtration filter device in FIG. 1. FIG. 5 is an enlarged sectional view of a part of FIG. 4.

As illustrated in FIG. 1 and FIG. 2, the filtration filter device according to the first exemplary embodiment includes a holding member 1, a tubular member 2 that is removably mounted on one main surface 1a (i.e., principal surface) of the holding member 1, and a tubular member 3 that is removably mounted on the other main surface 1b (i.e., the opposing principal surface) of the holding member 1.

As illustrated in FIG. 3 to FIG. 5, the holding member 1 is configured to hold an outer circumferential portion 4A of a filtration filter 4 that filters an object contained in a fluid. According to the first embodiment, the holding member 1 includes a first frame member 11 and a second frame member 12. The first frame member 11 and the second frame member 12 are configured to interpose the outer circumferential portion 4A of the filtration filter 4 therebetween.

More specifically, the first frame member 11 includes an annular flat plate 11a and an annular projecting portion 11c that projects toward the tubular member 2 around a central through-hole 11b. The diameter of the flat plate 11a is, for example, 18 mm. The thickness of the flat plate 11a is, for example, 1.5 mm. The height of the projecting portion 11c is, for example, 1.5 mm.

As further shown, an annular flange 11d that projects toward the center of the through-hole 11b is formed on the inner surface of the annular projecting portion 11c. The flange 11d is formed, for example, at a position 0.1 mm away from the top of the projecting portion 11c toward the flat plate 11a. The thickness of an end portion 11f of the flange 11d on the center side of the through-hole 11b decreases such that the flange 11d has an inclined surface 11e on the side facing the tubular member 3. In an exemplary aspect, the thickness of a portion of the flange 11d near the projecting portion 11c is, for example, 0.3 mm. The thickness of the end portion 11f of the flange 11d is, for example, 0.2 mm. The inclination angle of the inclined surface 11e is, for example, 45 degrees.

Moreover, as further shown, the second frame member 12 includes an annular flat plate 12a, an annular projecting portion 12c that projects toward the tubular member 2 around a central through-hole 12b, and an annular projecting portion 12d that projects toward the tubular member 3 around the central through-hole 12b.

In an exemplary aspect, the diameter of the flat plate 12a is, for example, 18 mm. The thickness of the flat plate 12a is, for example, 1.5 mm. The height of the projecting portion 12d is, for example, 1.5 mm.

The projecting portion 12c has an outer diameter that is slightly smaller than the diameter of the through-hole 11b such that the projecting portion 12c can be inserted in the through-hole 11b of the first frame member 11. The shape of an end portion 12f of the projecting portion 12c matches the shape of the flange 11d on the side facing the tubular member 3. That is, the end portion 12f has an inclined surface 12e that corresponds to the inclined surface 11e.

As illustrated in FIG. 4, the filtration filter 4 is held with a tensile force applied thereto in a surface direction in a manner in which the outer circumferential portion 4A is interposed between the flange 11d of the first frame member 11 and the end portion 12f of the projecting portion 12c of the second frame member 12 and extends along the inclined surface 11e and the inclined surface 12e. Moreover, the outer circumferential portion 4A of the filtration filter 4 is interposed at a position away from a central plane S1 with respect to the thickness direction of the holding member 1 in the thickness direction. Thus, as shown, the central plane S1 extends perpendicularly to the flow direction of the fluid through the filtration filter 4. Moreover, as shown in this first exemplary embodiment, the filtration filter 4 is disposed inside the annular projecting portion 11c. In addition, the filtration filter 4 is substantially flush with an opening plane S2 that is defined by the end portion of the annular projecting portion 11c.

As illustrated in FIG. 3, the flat plate 11a of the first frame member 11 has through-holes 11g each of which extends therethrough in the thickness direction. The through-holes 11g are arranged at regular intervals in the circumferential direction of the flat plate 11a. Similarly, the flat plate 12a of the second frame member 12 has through-holes 12g each of which extends therethrough in the thickness direction. The through-holes 12g are arranged at regular intervals in the circumferential direction of the flat plate 12a so as to correspond to the through-holes 11g. According to the exemplary aspect, fasteners (not illustrated) such as screws are inserted in the through-holes 11g and 12g with the projecting portion 12c of the second frame member 12 inserted in the through-hole 11b of the first frame member 11, and thus, the first frame member 11 and the second frame member 12 are secured to each other.

As further shown, the tubular member 2 includes an engagement portion 2a that can engage the projecting portion 11c of the first frame member 11. The tubular member 2 is removably mounted on the first frame member 11 in a manner in which the engagement portion 2a engages the outer circumferential surface of the projecting portion 11c of the first frame member 11. The tubular member 2 includes a hollow portion 2b configured as a channel through which the fluid flows. The tubular member 2 is mounted on the first frame member 11 such that the hollow portion 2b faces at least a part of one main surface of the filtration filter 4. This enables the fluid to be supplied to the filtration filter 4 via the hollow portion 2b that serves as the fluid inflow channel. Alternatively, the fluid that has passed through the filtration filter 4 can be discharged via the hollow portion 2b that serves as the fluid discharge channel.

The tubular member 2 includes a Luer lock connector 2c according to an exemplary aspect. Preferably, the Luer lock connector 2c has a form that meets a standard such as ISO594-2. According to the first embodiment, the connector 2c is formed of an annular projecting portion that projects outward from an end portion of the tubular member 2. For example, the tubular member 2 is mounted on a Luer lock syringe in a manner in which the connector 2c is screwed along a spiral groove (not illustrated) that is formed on the inner circumferential surface of a hollow end portion of the Luer lock syringe.

According to the first embodiment, the tubular member 3 has the same structure as the tubular member 2. Specifically, the tubular member 3 includes an engagement portion 3a that can engage the projecting portion 12d of the second frame member 12. The tubular member 3 is removably mounted on the second frame member 12 in a manner in which the engagement portion 3a engages the outer circumferential surface of the projecting portion 12d of the second frame member 12. The tubular member 3 includes a hollow portion 3b that serves as a channel through which the fluid flows. The tubular member 3 is mounted on the second frame member 12 such that the hollow portion 3b faces at least a part of the other main surface of the filtration filter 4. This enables the fluid to be supplied to the filtration filter 4 via the hollow portion 3b that serves as the fluid inflow channel. Alternatively, the fluid that has passed through the filtration filter 4 can be discharged from the hollow portion 3b that serves as the fluid discharge channel.

Similarly, the tubular member 3 includes a Luer lock connector 3c. Preferably, the Luer lock connector 3c has a form that meets a standard such as ISO594-2. According to the first embodiment, the connector 3c is formed of an annular projecting portion that projects outward from an end portion of the tubular member 3. For example, the tubular member 3 is mounted on a Luer lock syringe in a manner in which the connector 3c is screwed along a spiral groove (not illustrated) that is formed on the inner circumferential surface of a hollow end portion of the Luer lock syringe.

Examples of the materials of the first frame member 11, the second frame member 12, and the tubular members 2 and 3 include metals such as duralumin and aluminum and resins such as polyethylene, polystyrene, polypropylene, polycarbonate, polyacetal, and polyetherimide.

According to the first embodiment, the object to be filtered is a biological substance that a liquid contains. According to the exemplary aspect and for purposes of this disclosure, the "biological substance" is a substance derived from a living organism such as a cell (eukaryote), a bacterium (eubacteria), and a virus. Examples of the cell (eukaryote) include an ovum, a spermatozoon, an induced pluripotent stem cell (iPS cell), an ES cell, a stem cell, a mesenchymal stem cell, a mononuclear cell, a single cell, a cell mass, a floating cell, an adhesion cell, a nerve cell, a leukocyte, a lymphocyte, a cell for regenerative medicine, an autologous cell, a cancer cell, a circulating tumor cell (CTC), HL-60, HELA, and fungi. Examples of the bacterium (eubacteria) include a colon *bacillus* and a tubercle *bacillus*.

Figure 6:
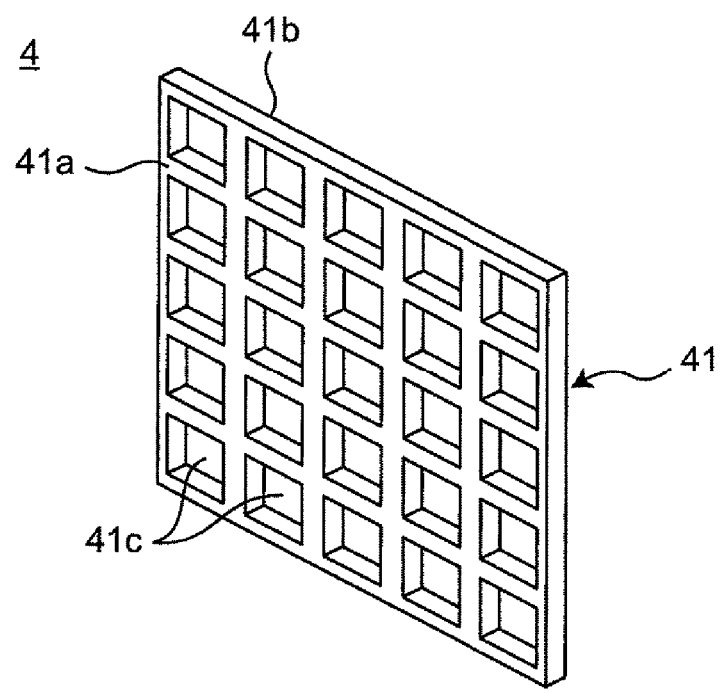
FIG. 6 schematically illustrates an enlarged sectional view of the structure of a part of a filtration filter.

FIG. 6 schematically illustrates an enlarged sectional view of the structure of a part of the filtration filter 4. As illustrated in FIG. 6, the filtration filter 4 includes a metallic porous film 41 that filters the object contained in the fluid.

As illustrated in FIG. 6, the metallic porous film 41 has a pair of main surfaces 41a and 41b that face each other. The metallic porous film 41 has through-holes 41c that extend between the main surfaces 41a and 41b. The through-holes 41c isolate biological substances from the liquid. The shape and dimensions of each through-hole 41c are appropriately determined in accordance with the shape and size of the biological substances. The through-holes 41c are arranged, for example, at regular intervals or in a periodical manner. For example, the shape of each through-hole 41c is a square when viewed from the main surface 41a of the metallic porous film 41. According to the first embodiment, the through-holes 41c are arranged in the form of a square lattice. The size of each through-hole 41c is, for example, no less than 0.1 µm and no more than 500 µm in length and no less than 0.1 µm and no more than 500 µm in width. The distance between the adjoining through-holes 41c is, for example, more than the diameter of the opening of each through-hole 41c and is equal to or less than 10 times the diameter of the opening, and is more preferably equal to or less than 3 times the diameter of the opening. An opening ratio of the through-holes 41c to the metallic porous film 41 is, for example, 10% or less.

Examples of the material of the metallic porous film 41 include gold, silver, copper, platinum, nickel, stainless steel, palladium, titanium, cobalt, an alloy thereof, and an oxide thereof. The dimensions of the metallic porous film 41 are, for example, 6 mm in diameter and no less than 0.1 µm and no more than 100 µm in thickness, preferably no less than 0.1 µm and no more than 50 µm in thickness. The shape of the metallic porous film 41 is, for example, circular, elliptic, or polygonal. According to the first embodiment, the shape of the metallic porous film 41 is circular. An outer circumferential portion of the metallic porous film 41 may have the through-holes 41c and may not have the through-holes 41c.

According to the first embodiment, the holding member 1 is configured to hold the outer circumferential portion 4A of the filtration filter 4, and the tubular members 2 and 3 are removably mounted on the holding member 1. With this structure, mounting the tubular members 2 and 3 on the holding member 1 enables the fluid to be supplied to the filtration filter 4 via the tubular member 2 or 3 to filter the object to be filtered. In addition, removing the tubular members 2 and 3 from the holding member 1 enables the object filtered and left on the filtration filter 4 to be directly observed while the holding member 1 holds the outer circumferential portion 4A of the filtration filter 4. At this time, the holding member 1 can maintain a state in which a tensile force is applied to the filtration filter 4, and accordingly, the filtration filter 4 can be inhibited from shaking and unintentionally moving. Since the state in which the tensile force is applied to the filtration filter 4 is maintained, focus can be readily adjusted when the object filtered and left on the filtration filter 4 is observed with, for example, an electron microscope. Furthermore, a user can move the filtration filter 4 by holding the holding member 1, and handling is easy. Accordingly, the above structure enables the object filtered and left on the filtration filter 4 to be more readily observed.

According to the first embodiment, the filtration filter 4 includes the metallic porous film 41 shown in FIG. 6. The use of the metallic porous film 41 enables both of the main surfaces to be inhibited or prevented from having irregularities. Accordingly, focus can be more readily adjusted when the object filtered and left on the filtration filter 4 is observed with, for example, an electron microscope.

According to the first exemplary embodiment, the holding member 1 includes the first frame member 11 and the second frame member 12 that are configured to interpose the outer circumferential portion 4A of the filtration filter 4 therebetween. With this structure, the filtration filter 4 can be readily replaced after the first frame member 11 and the second frame member 12 are separated from the outer circumferential portion.

According to the first embodiment, the first frame member 11 and the second frame member 12 interpose the outer circumferential portion 4A of the filtration filter 4 at a position away from the central plane S1 with respect to the thickness direction of the holding member 1 in the thickness direction. More specifically, the holding member 1 includes the annular projecting portion 11c that projects in the thickness direction from one main surface thereof, and the filtration filter 4 is disposed inside the projecting portion 11c. With this structure, for example, in the case where the hollow portion 2b of the tubular member 2 is used as the fluid inflow channel, the filtration filter 4 is located nearer to the side on which the fluid is supplied, and accordingly, focus can be readily adjusted when the object filtered and left on the filtration filter 4 is observed with, for example, an electron microscope. For example, when the hollow portion 2b of the tubular member 2 is used as the fluid discharge channel, the filtration filter 4 is located nearer to the side on which the fluid is discharged, and the volume of a space that is surrounded by the holding member 1 and the filtration filter 4 can be increased. This enables the fluid to be inhibited from overflowing from the space when the tubular member 2 is removed and enables the filtration filter 4 to filter the object to be filtered with more certainty. The first frame member 11 and the second frame member 12 more preferably interpose the outer circumferential portion 4A of the filtration filter 4 at a position closer than the central plane S1 with respect to the thickness direction of the holding member 1 to the one main surface 1a or the other main surface 1b.

According to the first embodiment, the filtration filter 4 is substantially flush with the opening plane S2 that is defined by the end portion of the annular projecting portion 11c. With this structure, focus can be more readily adjusted when the object filtered and left on the filtration filter 4 is observed with, for example, an electron microscope. In addition, the volume of the space that is surrounded by the holding member 1 and the filtration filter 4 can be further increased. This enables the filtration filter 4 to filter the object to be filtered with more certainty. The filtration filter 4 may be flush with the opening plane S2. In this case, the same effect as above can be achieved.

According to the first embodiment, the tubular member 3 is removably mounted on the other main surface 1b of the holding member 1. With this structure, for example, the hollow portion 2b of the tubular member 2 is configured as the fluid inflow channel, and the hollow portion 3b of the tubular member 3 is configured as the fluid discharge channel. This is also advantageous when the fluid is caused to flow in an opposite direction for backwashing. In addition, a symmetric structure in the vertical direction with the filtration filter 4 centered, for example, can be formed, and it is not necessary for a user to be careful that which portion is the fluid inflow channel or the fluid discharge channel when the filtration filter device is used.

According to the first embodiment, the tubular members 2 and 3 include the Luer lock connectors 2c and 3c. This structure enables and provides, for example, direct mounting on a Luer lock syringe and improves usability.

Figure 7:
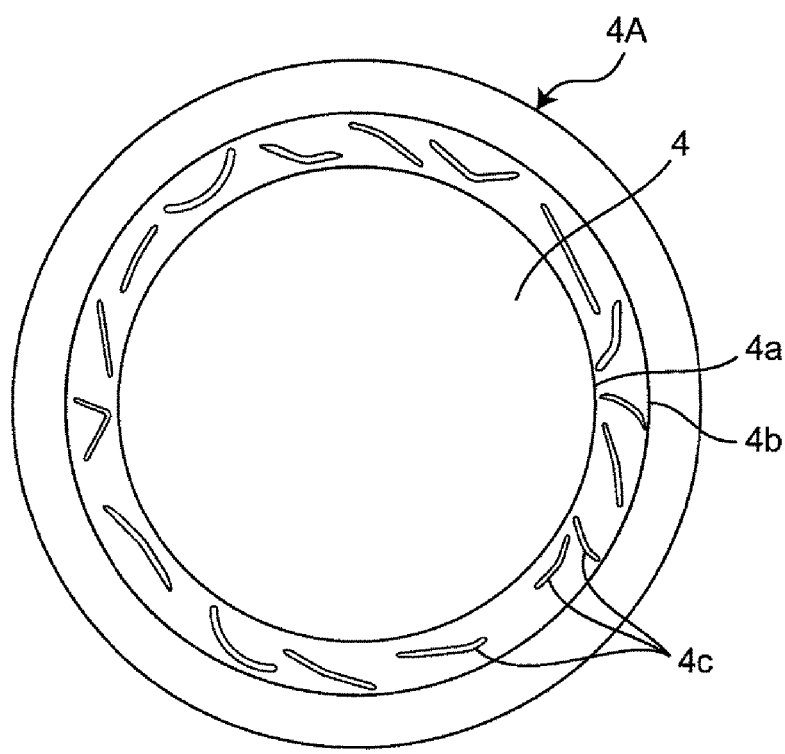
FIG. 7 schematically illustrates a plan view of a filtration filter according to a modification.

According to the first embodiment, as illustrated in FIG. 5, the inclined surface 11e of the first frame member 11 and the inclined surface 12e of the second frame member 12 interpose the outer circumferential portion 4A of the filtration filter 4 such that the outer circumferential portion 4A of the filtration filter 4 has a first bend 4a and a second bend 4b. At this time, as illustrated in FIG. 7, the outer circumferential portion 4A of the filtration filter 4 is preferably interposed such that there are striped projections 4c between the first bend 4a and the second bend 4b. With this structure, the striped projections 4c can increase frictional forces between the first frame member 11 and the outer circumferential portion 4A of the filtration filter 4 and between the second frame member 12 and the outer circumferential portion 4A of the filtration filter 4. This increases forces at which the first frame member 11 and the second frame member 12 hold the filtration filter 4 without increasing the number of components. Each striped projection 4c protrudes from the one main surface of the filtration filter 4 and that has a height that is 0.1 to 2 times the thickness of the filtration filter 4.

As illustrated in FIG. 7, the striped projections 4c are disposed between the first bend 4a and the second bend 4b. The striped projections 4c preferably extend in irregular directions. This structure can increase the frictional forces between the first frame member 11 and the outer circumferential portion 4A of the filtration filter 4 and between the second frame member 12 and the outer circumferential portion 4A of the filtration filter 4 and further increase the forces at which the first frame member 11 and the second frame member 12 hold the filtration filter 4.

The striped projections 4c may be formed of wrinkles of the metallic porous film 41. The terms "wrinkles" for purposes of this disclosure and as described herein means fine creases that are produced when the metallic porous film 41 becomes loose or shrinks. In this case, the metallic porous film 41 itself can form the striped projections 4c, and there is no need for additional members for the striped projections 4c.

It should be appreciated that the present disclosure is not limited to the above described exemplary embodiment and can be carried out with other embodiments. For example, in the above description, the object to be filtered is the biological substance that the liquid contains. The exemplary embodiment, however, is not limited thereto. Alternatively, the object to be filtered may be a substance contained in a gas. That is, the object to be filtered may be, for example, PM2.5 that air contains, provided that the object to be filtered is a substance contained in a fluid.

In the above description, the filtration filter 4 is used to filter biological substances from the liquid. The exemplary embodiments, however, is not limited thereto. For example, the filtration filter 4 may be used to concentrate a liquid. The filtration filter 4 is particularly useful as a cell culture filter because the object filtered and left on the filtration filter 4 can be more readily observed.

In the above description, the first frame member 11 and the second frame member 12 are secured to each other with the fasteners such as screws. However, the exemplary embodiment is not limited thereto. For example, the first frame member 11 and the second frame member 12 may be configured to engage each other and secured to each other without the fasteners.

In the above description, the tubular member 2 and the tubular member 3 have the same structure. However, the exemplary embodiment is not limited thereto. The tubular member 2 and the tubular member 3 may have different structures.

In the above description, the tubular member 2 is configured to be removably mounted on the one main surface 1a of the holding member 1. However, the exemplary embodiment is not limited thereto. For example, the tubular member 2 can be configured to be removably mounted on a side surface of the holding member 1.

In the above description, the tubular member 3 is removably mounted on the other main surface 1b of the holding member 1. However, the exemplary embodiment is not limited thereto. For example, the tubular member 3 can be configured to be removably mounted on a side surface of the holding member 1.

In the above description, the tubular member 2 is mounted on the first frame member 11 in a manner in which the engagement portion 2a of the tubular member 2 engages the projecting portion 11c of the first frame member 11. However, the exemplary embodiment is not limited thereto. It is only necessary for the tubular member 2 to be removably mounted on the first frame member 11, and the form thereof is not limited. For example, the first frame member 11 may include a locking pawl (for example, a hook-like pawl), the tubular member 2 may include a receiving portion (for example, a hole in which the hook-like pawl can fit), and the locking pawl and the receiving portion may engage each other.

For example, the engagement portion 2a of the tubular member 2 may has an internal thread, the projecting portion 11c of the first frame member 11 may has an external thread, and the external thread may be screwed in the internal thread. With this structure, the tubular member 2 can be more readily mounted on and removed from the holding member 1, and the liquid can be more successfully inhibited from leaking. In this case, it is preferable that the external thread of the first frame member 11 that is screwed in the internal thread of the tubular member 2 be prevented from being unscrewed due to a rotational force created when the connector 2c of the tubular member 2 is mounted on the Luer lock syringe.

For example, the inner diameter of the engagement portion 2a of the tubular member 2 is preferably larger than the outer diameter of the connector 2c. The materials and surface roughness, for example, are preferably determined such that the frictional force between the internal thread of the tubular member 2 and the external thread of the first frame member 11 is stronger than the frictional force between the connector 2c of the tubular member 2 and the Luer lock syringe.

Similarly, in the above description, the tubular member 3 is mounted on the second frame member 12 in a manner in which the engagement portion 3a of the tubular member 3 engages the projecting portion 12d of the second frame member 12. However, the exemplary embodiment is not limited thereto. It is only necessary for the tubular member 3 to be removably mounted on the second frame member 12, and the form thereof is not limited. For example, the second frame member 12 may include a locking pawl (for example, a hook-like pawl), the tubular member 3 may include a receiving portion (for example, a hole in which the hook-like pawl can fit), and the locking pawl and the receiving portion may engage each other.

For example, the engagement portion 3a of the tubular member 3 may has an internal thread, the projecting portion 12d of the second frame member 12 may has an external thread, and the external thread may be screwed in the internal thread. With this structure, the tubular member 3 can be more readily mounted on and removed from the holding member 1, and the liquid can be more successfully inhibited from leaking. In this case, it is preferable that the external thread of the second frame member 12 that is screwed in the internal thread of the tubular member 3 be prevented from being unscrewed due to a rotational force created when the connector 3c of the tubular member 3 is mounted on the Luer lock syringe. For example, the inner diameter of the engagement portion 3a of the tubular member 3 is preferably larger than the outer diameter of the connector 3c. The materials and surface roughness, for example, are preferably determined such that the frictional force between the internal thread of the tubular member 3 and the external thread of the second frame member 12 is stronger than the frictional force between the connector 3c of the tubular member 3 and the Luer lock syringe.

The tubular member 2 and the tubular member 3 are preferably mounted on the holding member 1 when the tubular member 2 and the tubular member 3 are rotated in opposite directions to screw the external thread of the projecting portion 11c of the first frame member 11 and the external thread of the projecting portion 12d of the second frame member 12 in the corresponding internal threads. With this structure, for example, when the tubular member 2 is removed from the holding member 1, the tubular member 3 can be inhibited from being rotated together with the tubular member 2 and unintentionally removed from the holding member 1.

The following description contains a preferable length in the direction of screwing, pitch, and number of winding of the internal threads of the tubular members 2 and 3 and the external threads of the holding member 1.

Table 1 below illustrates the results of evaluation of a liquid leak, work efficiency, and work time when 20 samples were manufactured such that the internal threads and the external threads that were screwed have different lengths in the direction of screwing and different pitches. In Table 1 below, the "number" means a sample number. The "diameter" means the outer diameter of each thread. The "length t" means the length in the direction of screwing. The "pitch P" means the distance between the tops of the threads or the distance between the bottoms of thread grooves in the direction of screwing. The millimeter is the unit of the "diameter", the "length t", and the "pitch P". The "number N of winding" means the number each thread is wound (that is, $N=t/P$). The "liquid leak (1 kpa)" represents the result of evaluation of whether a liquid leak in an amount exceeding a permissible level occurred between the external threads and the internal threads when pure water flowed to the filtration filter at a pressure of 1 kPa (kilopascal). The "liquid leak (100 kpa)" represents the result of evaluation of whether a liquid leak in an amount exceeding the permissible level occurred between the external threads and the internal threads when pure water flowed to the filtration filter at a pressure of 100 kPa. The "work efficiency" represents the result of evaluation of easiness of screwing when the external threads were screwed in the internal threads. The "work time" represents the result of evaluation of whether the time required for manually screwing the external threads in the internal threads in a glovebox was time (for example, 30 seconds) during which the activity of the cells decreased below a permissible level assuming that the object to be filtered is a cell.

the filtration filter at a high pressure of 100 kPa. Accordingly, $N (=t/P) \geq 1$ preferably holds, and $N (=t/P) \geq 2$ more preferably holds. This enables a liquid leak in an amount exceeding the permissible level to be inhibited from occurring between the external threads and the internal threads.

As illustrated in Table 1, in samples 7 and 15 in which the pitch P was 0.2 mm, it was difficult to screw the external threads in the internal threads. Accordingly, the pitch P is preferably 0.3 mm or more. This improves the work efficiency when the external threads are screwed in the internal threads.

As illustrated in Table 1, in samples 19 and 20 in which the length t was 5.0 mm, the time required for manually screwing the external threads in the internal threads in the glovebox exceeded the time during which the activity of the cells decreased below the permissible level.

Accordingly, the length t is preferably 4.0 mm or less. This shortens the work time during which the external threads are screwed in the internal threads and inhibits the activity of the cells from decreasing.

In the case where the pitch P is less than 0.3 mm, the work efficiency with which the external threads are screwed in the internal threads decreases even when the length t is 4.0 mm or less, and the work time is longer than expected. For this reason, the samples 7 and 15 are evaluated as a "fail" because the pitch P was less than 0.3 mm although the length t was 4.0 mm or less.

Table 2 below illustrates the results of evaluation of the liquid leak, the work efficiency, and the work time when 8 samples were manufactured such that the internal threads and the external threads that were screwed have different diameters, different lengths in the direction of screwing, and different pitches.

TABLE 1

| NUMBER | DIAMETER (mm) | LENGTH t (mm) | PITCH P (mm) | NUMBER N OF WINDING | LIQUID LEAK (1 kpa) | LIQUID LEAK (100 kpa) | WORK EFFICIENCY | WORK TIME |
|---|---|---|---|---|---|---|---|---|
| 1 | 12 | 1.0 | 0.3 | 3.3 | PASS | PASS | PASS | PASS |
| 2 | 12 | 1.0 | 0.5 | 2.0 | PASS | PASS | PASS | PASS |
| 3 | 12 | 1.0 | 1.0 | 1.0 | PASS | FAIL | PASS | PASS |
| 4 | 12 | 1.0 | 1.2 | 0.8 | FAIL | FAIL | PASS | PASS |
| 5 | 12 | 1.0 | 1.5 | 0.7 | FAIL | FAIL | PASS | PASS |
| 6 | 12 | 1.0 | 2.0 | 0.5 | FAIL | FAIL | PASS | PASS |
| 7 | 12 | 2.0 | 0.2 | 10.0 | PASS | PASS | FAIL | FAIL |
| 8 | 12 | 2.0 | 0.3 | 6.7 | PASS | PASS | PASS | PASS |
| 9 | 12 | 2.0 | 0.5 | 4.0 | PASS | PASS | PASS | PASS |
| 10 | 12 | 2.0 | 0.8 | 2.5 | PASS | PASS | PASS | PASS |
| 11 | 12 | 2.0 | 1.0 | 2.0 | PASS | PASS | PASS | PASS |
| 12 | 12 | 2.0 | 1.2 | 1.7 | PASS | FAIL | PASS | PASS |
| 13 | 12 | 2.0 | 1.5 | 1.3 | PASS | FAIL | PASS | PASS |
| 14 | 12 | 2.0 | 2.0 | 1.0 | PASS | FAIL | PASS | PASS |
| 15 | 12 | 4.0 | 0.2 | 20.0 | PASS | PASS | FAIL | FAIL |
| 16 | 12 | 4.0 | 0.3 | 13.3 | PASS | PASS | PASS | PASS |
| 17 | 12 | 4.0 | 1.0 | 4.0 | PASS | PASS | PASS | PASS |
| 18 | 12 | 4.0 | 2.0 | 2.0 | PASS | PASS | PASS | PASS |
| 19 | 12 | 5.0 | 0.3 | 16.7 | PASS | PASS | PASS | FAIL |
| 20 | 12 | 5.0 | 1.0 | 5.0 | PASS | PASS | PASS | FAIL |

As illustrated in Table 1, in samples 4 to 6 in which the number N of winding was less than 1, a liquid leak in an amount exceeding the permissible level occurred between the external threads and the internal threads when pure water flowed to the filtration filter at a pressure of 1 kPa. In samples 3 to 6 and 12 to 14 in which the number N of winding was less than 2, a liquid leak in an amount exceeding the permissible level occurred between the external threads and the internal threads when pure water flowed to

TABLE 2

| NUMBER | DIAMETER (mm) | LENGTH t (mm) | PITCH P (mm) | NUMBER N OF WINDING | LIQUID LEAK (1 kpa) | LIQUID LEAK (100 kpa) | WORK EFFICIENCY | WORK TIME |
|---|---|---|---|---|---|---|---|---|
| 21 | 22 | 2.0 | 0.2 | 10.0 | PASS | PASS | FAIL | FAIL |
| 22 | 22 | 2.0 | 0.3 | 6.7 | PASS | PASS | PASS | PASS |

TABLE 2-continued

| NUMBER | DIAMETER (mm) | LENGTH t (mm) | PITCH P (mm) | NUMBER N OF WINDING | LIQUID LEAK (1 kpa) | LIQUID LEAK (100 kpa) | WORK EFFICIENCY | WORK TIME |
|---|---|---|---|---|---|---|---|---|
| 23 | 22 | 2.0 | 0.5 | 4.0 | PASS | PASS | PASS | PASS |
| 24 | 22 | 2.0 | 1.0 | 2.0 | PASS | PASS | PASS | PASS |
| 25 | 22 | 2.0 | 1.5 | 1.3 | PASS | FAIL | PASS | PASS |
| 26 | 22 | 2.0 | 2.5 | 0.8 | FAIL | FAIL | PASS | PASS |
| 27 | 30 | 2.0 | 0.5 | 4.0 | PASS | PASS | PASS | PASS |
| 28 | 30 | 2.0 | 3.5 | 0.6 | FAIL | FAIL | PASS | PASS |

As illustrated in Table 2, in samples 21 to 28 in which the diameter was changed from that in the samples 1 to 20 in Table 1, the results of the liquid leak, the work efficiency, and the work time were the same as in the samples 1 to 20. Accordingly, it was confirmed that the diameter does not have effect on the preferable length in the direction of screwing, pitch, and number of winging of the internal threads and the external threads.

In the samples 1 to 28 illustrated in Tables 1 and 2, the material of the internal threads and the external thread was POM (polyacetal). Samples were manufactured in the same manner as in the samples 1 to 28 except that the material of the internal threads and the external threads was changed into acrylic. The samples achieved the same results of evaluation of the liquid leak, the work efficiency, and the work time. That is, it was confirmed that the material does not have effect on the preferable length in the direction of screwing, pitch, and number of winging of the internal threads and the external threads.

Second Embodiment

Figure 8:
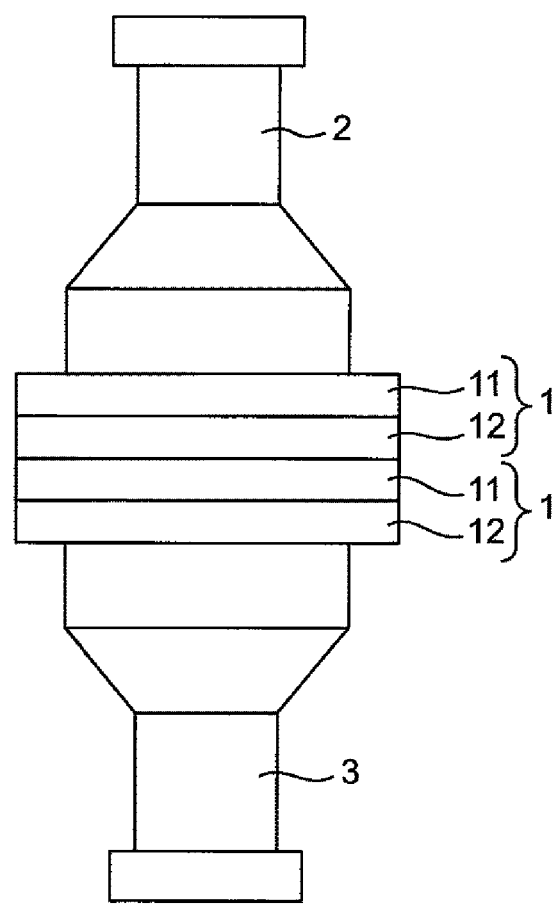
FIG. 8 is a side view of the overall structure of a filtration filter device according to a second exemplary embodiment.
Figure 9:
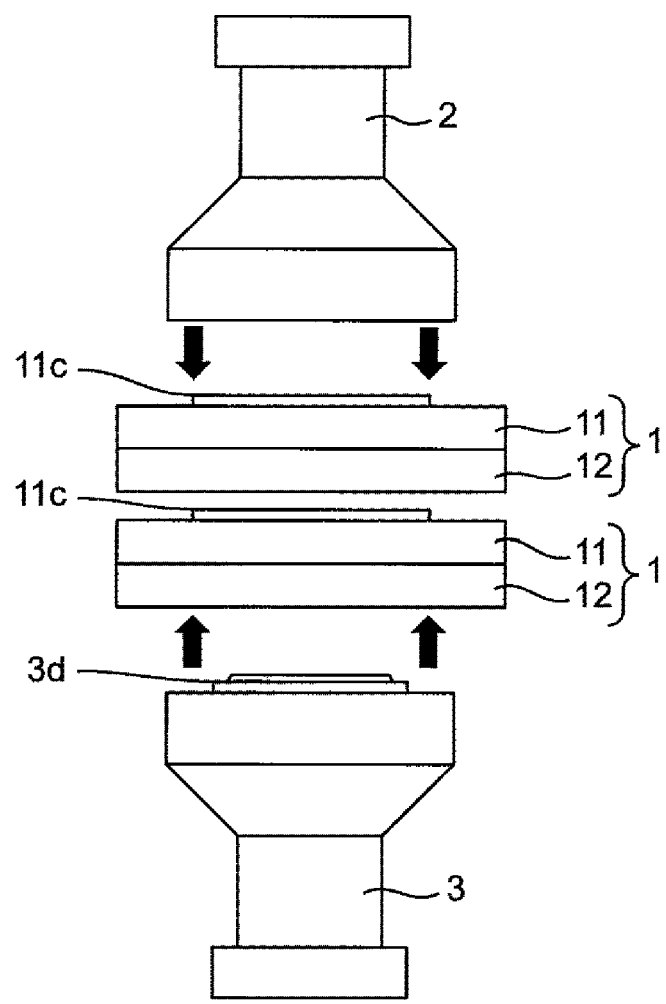
FIG. 9 is an exploded perspective view of a part of the filtration filter device in FIG. 8.

FIG. 8 is a side view of the overall structure of a filtration filter device according to a second exemplary embodiment of the present disclosure. FIG. 9 is an exploded perspective view of a part of the filtration filter device in FIG. 8.

The filtration filter device according to the second exemplary embodiment differs from the filtration filter device according to the first exemplary embodiment by providing two holding members 1 as shown in FIG. 8. Components like or similar to the components described according to the first exemplary embodiment are designated by like reference numbers, and a duplicated description is omitted.

The two holding members 1 are removably mounted on each other. According to the second embodiment, one of the second frame members 12 removably engages the projecting portion 11c of the first frame member 11 of the holding member 1 adjacent thereto, and the other removably engages a projecting portion 3d of the tubular member 3.

According to the second embodiment, two filtration filters 4 can be readily installed in and removed from the filtration filter device that includes the two holding members 1 that are mountable on and removable from each other, and the usability can be improved. For example, the object to be filtered can be filtered with the two filtration filters 4, and accordingly, the filtering efficiency can be improved. In the case where the diameter of each through-hole is changed between the filtration filters 4 that are held by the holding members 1, objects to be filtered having different sizes can be classified.

According to the second embodiment, the filtration filter device includes the two holding members 1. However, the exemplary embodiment is not limited thereto. It should be appreciated that the filtration filter device may include three or more holding members 1. The usability can be greatly improved in a manner in which the number and order of the holding members 1 and the kind (for example, the diameter of each through-hole, the opening ratio, and the material) of the filtration filters 4 are made optionally changeable depending on the object to be filtered.

Third Embodiment

Figure 10:
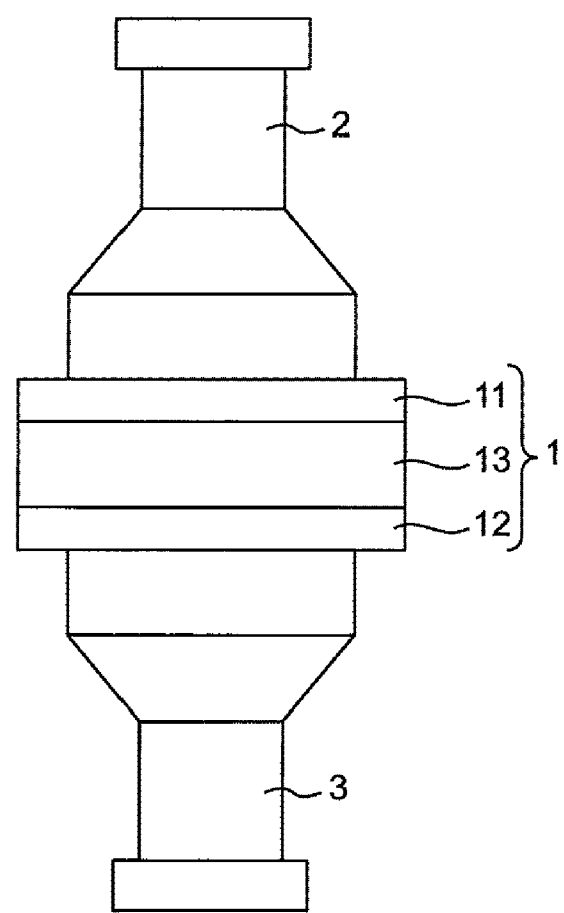
FIG. 10 is a side view of the overall structure of a filtration filter device according to a third exemplary embodiment.
Figure 11:
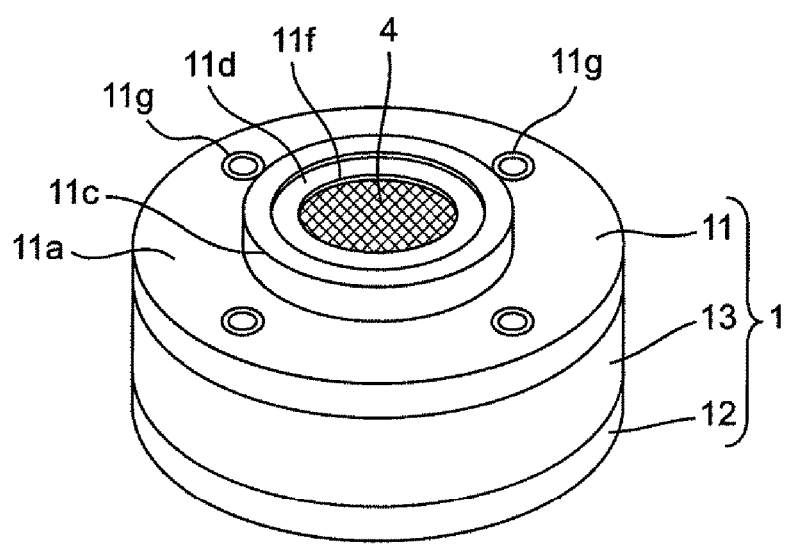
FIG. 11 is a perspective view of a holding member that the filtration filter device in FIG. 10 includes.
Figure 12:
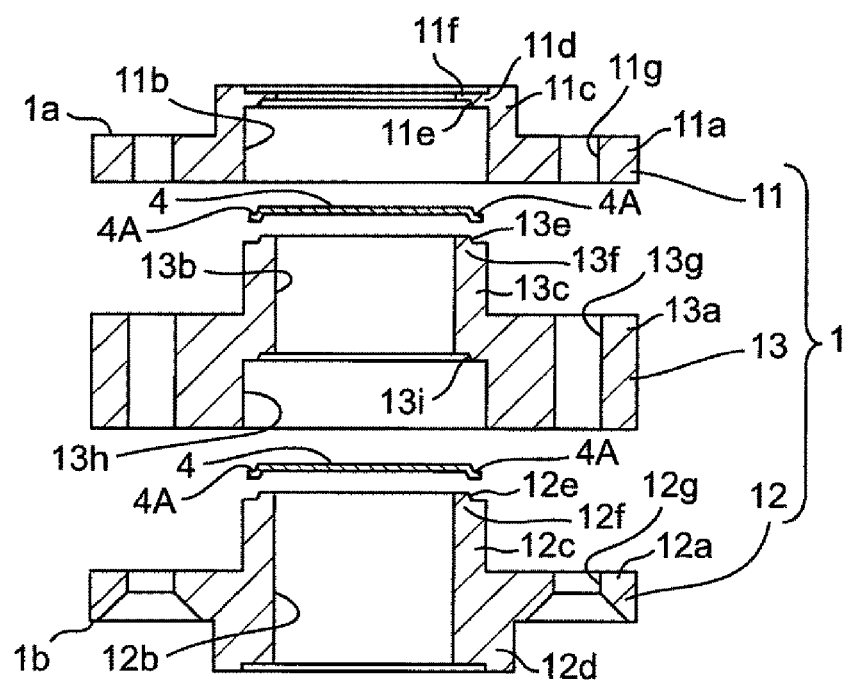
FIG. 12 is an exploded perspective view of the holding member in FIG. 11.

FIG. 10 is a side view of the overall structure of a filtration filter device according to a third exemplary embodiment of the present disclosure. FIG. 11 is a perspective view of a holding member that the filtration filter device in FIG. 10 includes. FIG. 12 is an exploded perspective view of the holding member in FIG. 11.

The filtration filter device according to the third exemplary embodiment differs from the filtration filter device according to the first exemplary embodiment discussed above in that the holding member 1 includes a third frame member 13 between the first frame member 11 and the second frame member 12. Components like or similar to the components described according to the first embodiment are designated by like reference numbers, and a duplicated description is omitted.

As illustrated in FIG. 11 or FIG. 12, the third frame member 13 includes an annular flat plate 13a and an annular projecting portion 13c that projects toward the first frame member 11 around a central through-hole 13b. The diameter of the flat plate 13a is, for example, 18 mm. The thickness of the flat plate 13a is, for example, 2.5 mm. The height of the projecting portion 13c is, for example, 1.5 mm.

The projecting portion 13c has the same structure as the projecting portion 12c of the second frame member 12. That is, the projecting portion 13c has an outer diameter that is slightly smaller than the diameter of the through-hole 11b such that the projecting portion 13c can be inserted in the through-hole 11b of the first frame member 11. The shape of an end portion 13f of the projecting portion 13c matches the shape of the flange 11d on the side facing the second frame member 12. That is, the end portion 13f has an inclined surface 13e that corresponds to the inclined surface 11e.

Moreover, according to the exemplary embodiment, at least one of the filtration filters 4 is held with a tensile force applied thereto in the surface direction in a manner in which the outer circumferential portion 4A is interposed between the flange 11d of the first frame member 11 and the end portion 13f of the projecting portion 13c of the third frame member 13 and extends along the inclined surface 11e and the inclined surface 13e.

The third frame member 13 includes an enlarged-diameter portion 13h at which a part of the central through-hole 13b is expanded such that the part has a diameter equal to the diameter of the through-hole 11b of the first frame member 11. The enlarged-diameter portion 13h includes a step portion 13i the shape of which matches the shape of the end portion 12f of the second frame member 12.

The other filtration filter 4 is held with a tensile force applied thereto in the surface direction in a manner in which the outer circumferential portion 4A is interposed between the step portion 13i of the third frame member 13 and the end portion 12f of the projecting portion 12c of the second frame member 12 and extends along the inclined surface 12e.

As illustrated in FIG. 12, the flat plate 13a of the third frame member 13 has through-holes 13g each of which extends therethrough in the thickness direction. The through-holes 13g are arranged at regular intervals in the circumferential direction of the flat plate 13a so as to correspond to the through-holes 11g and 12g. The end portion 13f of the projecting portion 13c of the third frame member 13 is inserted in the through-hole 11b of the first frame member 11. The end portion 12f of the projecting portion 12c of the second frame member 12 is inserted in the enlarged-diameter portion 13h of the third frame member 13. In this state, fasteners (not illustrated) such as screws are inserted in the through-holes 11g, 13g, and 12g, and thus, the first frame member 11, the third frame member 13, and the second frame member 12 are secured to each other.

Examples of the material of the third frame member 13 include metals such as duralumin and aluminum and resins such as polyethylene, polystyrene, polypropylene, polycarbonate, polyacetal, and polyetherimide.

According to the third exemplary embodiment, the holding member 1 includes the three frame members of the first frame member 11, the second frame member 12, and the third frame member 13, and the outer circumferential portion 4A of each filtration filter 4 can be interposed between the adjoining frame members. With this structure, the two filtration filters 4 can be readily installed in and removed from the filtration filter device, and the usability can be improved. For example, the object to be filtered can be filtered with the two filtration filters 4, and accordingly, the filtering efficiency can be improved. In the case where the diameter of each through-hole is changed between the filtration filters 4 that are held by the holding members 1, objects to be filtered having different sizes can be classified.

According to the third exemplary embodiment, the filtration filters 4 are disposed between the first frame member 11 and the third frame member 13 and between the third frame member 13 and the second frame member 12. However, the exemplary embodiment is not limited thereto. The filtration filters 4 may be disposed between the first frame member 11 and the third frame member 13 or between the third frame member 13 and the second frame member 12. For example, in the case where the filtration filters 4 are disposed between the third frame member 13 and the second frame member 12, the volume of a space between the filtration filters 4 and the tubular member 2 can be increased. This enables the fluid to be inhibited from overflowing from the space when the tubular member 2 is removed. In other words, the through-hole 13b of the third frame member 13 can function as a buffer that temporally stores the fluid. This enables the filtration filters 4 to filter the object to be filtered with more certainty.

According to the third exemplary embodiment, the holding member 1 includes the three frame members of the first frame member 11, the second frame member 12, and the third frame member 13, and the outer circumferential portion 4A of each filtration filter 4 can be interposed between the adjoining frame members. However, the exemplary embodiment is not limited thereto. The holding member 1 may include four or more frame members, and the outer circumferential portion 4A of each filtration filter 4 may be interposed between the adjoining frame members.

It should be further appreciated that an appropriate combination of embodiments among the above embodiments can achieve the same effects as the embodiments achieve.

Although the exemplary embodiments of the present invention are sufficiently described with reference to the accompanying drawings, various modifications and alterations are obvious for a person skilled in the art. It should be understood that the modifications and alterations are included in the present invention recited by the accompanying claims without departing from the scope of the present invention.

It should further be appreciated that the present disclosure is useful as a filtration filter device that filters the object to be filtered that the fluid contains, such as biological substances or PM2.5 because the object filtered and left on the filtration filter can be more readily observed.

REFERENCE SIGNS LIST 1 holding member
1a one main surface
1b the other main surface
2 tubular member
2a engagement portion
2b hollow portion
2c connector (Luer lock connector)
3 tubular member
3a engagement portion
3b hollow portion
3c connector (Luer lock connector)
4 filtration filter
4A outer circumferential portion
4a first bend
4b second bend
4c striped projection
11 first frame member
11a flat plate
11b through-hole
11c projecting portion
11d flange
11e inclined surface
11f end portion
11g through-hole
12 second frame member
12a flat plate
12b through-hole
12c projecting portion
12d projecting portion
12e inclined surface
12f end portion
12g through-hole
13 third frame member
13a flat plate
13b through-hole
13c projecting portion
13e inclined surface
13f end portion
13g through-hole
13h enlarged-diameter portion
13i step portion
41 metallic porous film
41a, 41b main surface
41c through-hole

The invention claimed is:

1. A filter device comprising:
   a filtration filter configured to filter an object contained in a fluid;
   a holding member configured to hold an outer circumferential portion of the filtration filter; and
   a tubular member configured to be removably mounted on the holding member such that a hollow portion of the tubular member that is configured as a channel through which the fluid flows faces at least a portion of a main surface of the filtration filter,
   wherein the holding member comprises a first frame member and a second frame member that are configured to interpose the outer circumferential portion of the filtration filter therebetween,
   wherein the first frame member and the second frame member are configured to interpose the outer circumferential portion of the filtration filter at a position away from a central plane relative to a thickness direction of the holding member, the thickness direction being in a flow direction of the fluid in the channel of the hollow portion, and
   wherein each of the first and second frame members further comprises an annular projecting portion that projects in a same direction as each other and in the thickness direction from respective main surfaces thereof, and wherein the filtration filter is disposed inside the respective annular projecting portions of the first and second frame members.

2. The filter device according to claim 1, wherein the filtration filter comprises a metallic porous film.

3. The filter device according to claim 1, wherein the filtration filter is flush with an opening plane that is defined by an end portion of the annular projecting portion of the second frame member.

4. The filter device according to claim 1, wherein the outer circumferential portion of the filtration filter includes a first bend and a second bend and is held between the first and second frame members.

5. The filter device according to claim 4, wherein the filtration filter comprises at least one striped projection disposed between the first bend and the second bend and configured to increase frictional force therebetween.

6. The filter device according to claim 5, wherein the at least one striped projection is a plurality of striped projections that extend in irregular directions relative to each other.

7. The filter device according to claim 1, wherein the tubular member is configured to be removably mounted on a first principal surface of the holding member, and the filter device comprises another tubular member configured to be removably mounted on a second principal surface of the holding member that opposes the first principal surface.

8. The filter device according to claim 1, wherein the tubular member comprises a Luer lock connector.

9. The filter device according to claim 1, further comprising a plurality of the holding members that are configured to be removably mounted on each other.

10. The filter device according to claim 1, wherein the filtration filter comprises a plurality of filters and the holding member further comprises at least three or more frame members that are each configured to interpose the outer circumferential portion of respective filters of the plurality of filters between adjoining frame members of the at least three or more frame members.

11. The filter device according to claim 1, wherein the tubular member has an internal thread, the holding member has an external thread, and the tubular member is configured to be removably mounted on the holding member when the external thread is screwed in the internal thread.

12. The filter device according to claim 11,
    wherein the tubular member is configured to be removably mounted on a first principal surface of the holding member,
    wherein the filter device comprises another tubular member configured to be removably mounted on a second principal surface of the holding member that opposes the first principal surface, and
    wherein the tubular member is mounted on the first principal surface and the other tubular member is mounted on the second principal surface when the respective tubular members are rotated in opposite directions to screw an external thread disposed on one main surface side of the holding member and an external thread disposed on another main surface side of the holding member in the corresponding internal threads.

13. The filter device according to claim 11, wherein $t/P \geq 1$ is satisfied, and wherein t is a length of the internal thread or the external thread in a direction of screwing, and P is a pitch of the internal thread or the external thread.

14. The filter device according to claim 11, wherein $t/P \geq 2$ is satisfied, and wherein t is a length of the internal thread or the external thread in a direction of screwing, and P is a pitch of the internal thread or the external thread.

15. The filter device according to claim 11, wherein a pitch of the internal thread or the external thread is at least 0.3 mm.

16. The filter device according to claim 15, wherein a length of the internal thread or the external thread in a direction of screwing is 4.0 mm or less.

17. The filter device according to claim 1,
    wherein the first frame member comprises an annular flange that projects towards a center of the first frame member, with the annular flange have an inclined surface relative to the central plane,
    wherein the annular projection portion of the second frame member that includes an end portion having an inclined surface that corresponds to the inclined surface of the annular flange of the first frame member, and
    wherein the filtration filter is held with a tensile force applied thereto between the annular flange of the first frame member and the end portion of the annular projection portion of the second frame member.

* * * * *